(12) United States Patent
Maznichenko et al.

(10) Patent No.: US 9,068,890 B2
(45) Date of Patent: Jun. 30, 2015

(54) THREE-DIMENSIONAL TITANIA NANO-FIBROUS ARCHITECTURE FOR MOLECULAR DETECTION BY RAMAN SPECTROSCOPY

(71) Applicants: Dmitry Maznichenko, Thornhill (CA); Krishnan Venkatakrishnan, Toronto (CA); Bo Tan, Toronto (CA)

(72) Inventors: Dmitry Maznichenko, Thornhill (CA); Krishnan Venkatakrishnan, Toronto (CA); Bo Tan, Toronto (CA)

( * ) Notice: Subject to any disclaimer, the term of this patent is extended or adjusted under 35 U.S.C. 154(b) by 97 days.

(21) Appl. No.: 14/030,740

(22) Filed: Sep. 18, 2013

(65) Prior Publication Data

US 2015/0077743 A1  Mar. 19, 2015

(51) Int. Cl.
*G01J 3/44* (2006.01)

(52) U.S. Cl.
CPC .......................................... *G01J 3/44* (2013.01)

(58) Field of Classification Search
USPC ................................................. 356/300–334
See application file for complete search history.

(56) References Cited

U.S. PATENT DOCUMENTS

2012/0086021 A1* 4/2012 Wang ............................. 257/84

* cited by examiner

*Primary Examiner* — Abdullahi Nur
(74) *Attorney, Agent, or Firm* — Quarles & Brady, LLP

(57) ABSTRACT

Disclosed herein is an optical molecular sensor, as well as methods and uses for such sensors in optical and medical devices. The sensor is based on traditionally inactive, limited or a combination thereof, materials that are regarded as such within surface-enhanced Raman spectroscopy (SERS). The disclosed invention essentially includes the said material or materials as the substrate, micro-pattern features developed from the substrate, and a three-dimensional (3D) architecture of nanoparticle fibers that generally surround and envelop the micro-pattern features. The nanoparticle fibers are specifically designed to have a desirable 3D network depth and porosity, as well as nanoparticle average diameter, standard deviation, and nanoparticle separation (i.e. nanogap), as well as nanoparticle crystal phase composition, stoichiometry, and crystallinity.

20 Claims, 5 Drawing Sheets

THREE-DIMENSIONAL TITANIA NANO-FIBROUS ARCHITECTURE FOR MOLECULAR DETECTION BY RAMAN SPECTROSCOPY

FIELD

The present disclosure relate to the fields of molecular detection, characterization or a combination thereof, using Raman spectroscopy. More specifically, this disclosure pertains to optical and medical sensor devices for detection of analytes that are formed on a titanium substrate, a traditionally SERS (Surface Enhanced Raman Spectroscopy) inactive material.

BACKGROUND

Testing for substance properties is integral to any science. This step was traditionally destructive in nature. Examples include pulling a metal apart until fracture to determine its strength, combusting a chemical to determine its elemental composition and digesting food to determine its toxicity. Such methods are not practical when considering substances that are expensive, limited in availability, substantially large or small, statistically variable and those which can additionally yield undesirable by-products resulting from destructive testing. To that effect, non-destructive testing (NDT) is a widely favored method. One of the most powerful NDT techniques is Raman spectroscopy.

Raman spectroscopy is a mature scientific method that can offer characterization of any substance in any physical state in addition to real-time reaction process monitoring. Raman spectroscopy relies on molecular vibrations that uniquely scatter the incident electromagnetic radiation. Since vibration is highly dependent on boundary constraints, it is possible to characterize crystal lattice structures and compositions of matter quite effectively. However, the scattering intensity due to these molecular vibrations may be too weak to detect even with sophisticated Raman equipment. As a result, a constantly increasing effort is being made to enhance the Raman scattering signal.

To enhance the Raman scattering signal, it was found that the materials' electronic structure holds most of the potential. That is, the collective oscillation or resonance of conductive band electrons can stimulate an electromagnetic enhancement. It was found that gold (Au) and silver (Ag) possess such desirable electronic structures. To localize this resonance condition, it was necessary to confine the surface plasmons to features that are smaller than the wavelength of incident light (i.e. to nanostructures). As a result, enhancement factors on the order of $10^4$ have now become available with Au and Ag nanoparticles (NPs). The field of study to enhance the Raman spectra is now commonly referred to as Surface Enhanced Raman Spectroscopy (SERS).

The current state of the art in Raman spectroscopy, as has been for decades, is to use single Au and Ag nanoparticles to enhance the acquired spectrum. Well-developed two-dimensional (2-D) nanomanufacturing techniques have shown Raman enhancement but with drawbacks. For example, recently published chemical methods to control NP aggregation demand precise solution control while commonly requiring additional stabilizers to regulate surface features. Stabilization is even more critical for bigger Au NPs. Modifying the solution and functionalizing the NPs in this way may also interfere and mislead the acquired Raman spectrum. Consequently, smaller Au NPs are used despite worse SERS performance. Alternatively, using Ag can improve SERS performance but the inherent oxide layer causes severe response fluctuations. Moreover, the highest plasmonic activity of Ag is at around the 532 nm excitation wavelength. This regime is highly susceptible to sample fluorescence and Raman signal deterioration.

Moreover, health and environmental impacts of nanotechnology, to date, have not been evaluated. This is potentially a serious problem for the future of SERS and Raman spectroscopy in general should it become apparent that Au and Ag NP containing systems are detrimental to human well-being in which case new SERS materials would need to be developed. As an alternative, titania is thermodynamically stable, attracts water and water soluble molecules, it is favorable for biomolecular bonding and it is corrosion resistant with a stable oxide surface. These characteristics are also favorable for SERS since the system has to remain stable under laser excitation. It is also desired for the targeted molecules to be in close proximity to the regions of surface enhanced electromagnetism. In general, titania is already a widely commercially available material, being used in cosmetics, pigments, water treatment, solar energy conversion and ultra-violet ray blocking. Manufacturing benefits such as cost, sustainability, high production and efficiency may be realized. TiO nanowires are already used in some medical devices to enhance surface cellular functions as disclosed by U.S. Pat. Publication No. 20050221072 and U.S. Pat. Publication No. 20050038498.

SUMMARY

The present disclosure teaches how to develop a traditionally SERS inactive material, titanium, to compete with the enhancement of the most popular plasmonic materials used widely in SERS. For example, traditionally SERS inactive titanium substrate has been developed to compete with the Raman enhancement of the industry dominant Au and Ag.

The sensor is developed on a titanium substrate using pulsed laser irradiation to produce a textured surface. The titanium surface, upon being irradiated by the pulsed laser beam, is partially transformed into titania micro-structures and nano-features. This synthesis method may be performed under ambient conditions in air, or the pressure may be varied from atmosphere. The synthesis parameters may be varied for sensor performance optimization. Subsequent application for Raman spectroscopy may make use of single-point, array, continuous scan or image based irradiation.

An embodiment includes an optical sensor for use with laser excitation and a Raman spectroscopy detector for detecting the presence of chemical groups, bio-molecular groups or a combination thereof, when exposed to the sensor. The sensor includes a titanium substrate, micro-pattern features developed on the titanium substrate, and three-dimensional nano-structures that generally surround and envelop the micro-pattern features. The micro-pattern features maybe in the form of vias, open channels, enclosed channels, junctions, locally oxidized surfaces, or any combination thereof. The nano-structures are nanofibers.

In the case of nanofibers as defined in this disclosure, nanoparticles (NPs) may be spread across the substrate surface and particularly over the "micro-pattern features" on the substrate in varying degrees of organization and dimensional structuring. For example, the NPs may be weakly interacting entities that are spaced randomly in a single layer. As another example, the NPs may be strongly interacting entities that form web structures in 3D space. These aforementioned strong NP interactions are usually not facilitated by any chemical additions or reagents but by the laser ablation plasma dynamics as disclosed herein. The 3D structuring also provides an extra laser confocal volume for improved detection of chemical compounds. The device is capable of detecting an analyte with a conservative Raman enhancement factor of up to but not limited to $10^6$, making it directly competitive to commercial Au and Ag based SERS devices.

In practicing the disclosed analyte detection method, molecules of the analyte are exposed to the sensor, the sensor surface is irradiated with a laser, and the resulting Raman information is acquired. The Raman equipment may acquire data from a single irradiated spot. The Raman equipment may also acquire data from a field of view or a scan that essentially provides spatial information. Spatial information may be preferred for SERS to reduce the dependency on regularly ordered "hot-spots" or regions of local electromagnetic enhancement. The data acquisition may also repeat in time.

An embodiment provides a method of producing a titanium based Surface Enhance Raman Scattering (SERS) sensor, comprising:

providing a titanium substrate having a surface and producing an array of sensor locations in a predefined portion of the surface by irradiating the predefined portion of the surface in the presence of air with laser pulses having an intensity, a wavelength, a pulse duration, an effective irradiation time and a pulse repetition rate selected to produce, at each sensor location, a micro-pattern feature in the surface of the substrate and a self-supported web structure that generally surround and envelop the micro-pattern feature, said self-supported web structured being made of nanofibers each comprised of a plurality of titanium based nanoparticles aligned into said self-supported web structure, wherein said array of sensor locations exhibit SERS activity.

There is also provided a titanium based Surface Enhance Raman Scattering (SERS) sensor, comprising:

a titanium substrate having a surface and an array of sensor locations located in a predefined portion of the surface, each of said sensor locations including a micro-pattern feature in the surface of the substrate and nanofibers that generally surround and envelop the micro-pattern feature, said nanofibers being comprised of a plurality of titanium based nanoparticles aligned into a self-supported web structure, wherein said array of sensor locations exhibit SERS activity.

There is provided a Raman spectroscopy based method of detecting an analyte, comprising the steps of:

a) providing a titanium substrate having a surface and producing thereon a sensor including an array of sensor locations in a predefined portion of the surface by irradiating the predefined portion of the surface with laser pulses having an intensity, a wavelength, a pulse duration, an effective irradiation time and a pulse repetition rate selected to produce, at each sensor location, a micro-pattern feature in the surface of the substrate and titanium based nanofibers that generally surround and envelop the micro-pattern feature, said nanofibers being comprised of a plurality of titanium based nanoparticles aligned into a self-supported web structure, wherein said array of sensor locations exhibit SERS activity; and b) exposing said sensor to a sample being tested for the presence of said analyte and thereafter recording a Raman spectra after irradiating the analyte sensor with a laser beam and correlating said Raman spectra to a characteristic Raman spectra of the analyte to determine the presence or absence of the analyte in the sample.

There is also provided a titanium based Surface Enhance Raman Scattering (SERS) system, comprising:

a) a sensor including a titanium substrate having a surface and an array of sensor locations located in a predefined portion of the surface, each of said sensor locations including a micro-pattern feature in the surface of the substrate and nanofibers that generally surround and envelop the micro-pattern feature, said nanofibers being comprised of a plurality of titanium based nanoparticles aligned into a self-supported web structure, wherein said array of sensor locations exhibit SERS activity;

b) a sample cell for receiving said sensor, said sample cell being configured to allow exposure of said sensor to a fluid being tested for the presence of an analyte;

c) a laser source for illuminating said array of sensor locations with laser light; and d) a detector for detecting laser light scattered from said sensor post exposure of said sensor to said fluid.

A further understanding of the functional and advantageous aspects of the present disclosure can be realized by reference to the following detailed description and drawings.

BRIEF DESCRIPTION OF THE DRAWINGS

The embodiments of the present disclosure are described with reference to the attached figures, wherein.

DETAILED DESCRIPTION

Definitions

Figure 1:
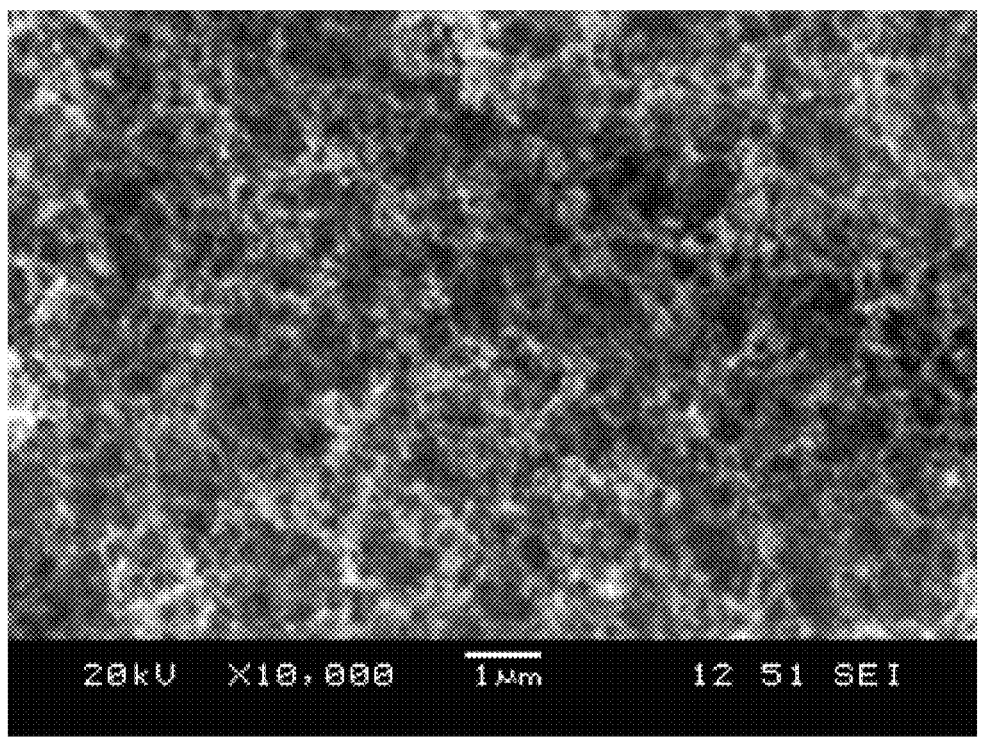
FIG. 1 is a scanning electron microscopy (SEM) image of the 3D titania nanofibrous network; the particular network shown is generated at a laser pulse repetition rate of 13 MHz and an irradiation time of 20 msec; other variations of laser repetition rate and irradiation time yield similar SEM images, with variations in nanofibrous porosity, 3D network depth and the total affect on the substrate (e.g. depth of the micro-vias, micro-via rim height etc.).

The terms below have the following meaning in this disclosure, unless otherwise indicated.

As used herein, the term "analyte" refers to a substance, whether in the form of a solid, liquid, or gas that is being detected by the sensor disclosed herein. This substance may be purely chemical, biological, radioactive, or any combination thereof, as present in nature or produced under synthetic conditions. The analyte may contain a single species of molecule or mixtures of different molecules. It may also be possible such that all or only select molecules are of Raman detection interest within the analyte.

As used herein, the term "containment" refers to the environmental surroundings of the material that is to be developed as a sensor by the disclosed pulsed laser method described herein.

As used herein, the term "nanofibers" refer to structures that are made of generally spherical NPs and interact in a manner so as to arrange themselves into single-strand or multi-strand elongate structures (nanofibers) that form a multiplicity of porous web-like features having the capability of supporting themselves in a 3D structure. The NPs may exhibit weak forces, e.g. NP charge, van der Waals etc. which allow the strands to exist with the NPs not physically bound to each other but may be separated by up to about 1 nm while maintaining their overall morphology. These forces are more dominant in the nanofiber network. If the NPs exhibit "strong forces", this means they may be physically bound by the NPs being sintered to their neighbors, cohesion etc. where the NPs cannot be separated without resulting morphological changes. Both of these concepts are represented with FIG. 5 feature 200 and feature 260 respectively. The nanofibers may include both weak and strong forces in the same nanofiber.

It may be possible that multiple NP size distributions exists within the nanofiber strands. The nanofibers may also have spatially varying solid material phases of the same elemental composition.

As used herein, the phrase "plasmonic material" in the context of SERS refers to a composition of physical matter that to date has been regarded to exhibit preferable plasmonic properties. The most popular plasmonic materials include Au and Ag which act to significantly enhance the Raman scattering intensity by the collective oscillation of conductive band electrons upon excitation with a laser.

As used herein, the phrase "regular material", "limited material", or "inactive material" in the context of SERS refers to a composition of physical matter that to date has been regarded to exhibit limited or inactive plasmonic properties. This regular material, being titanium as disclosed herein, can be oxidized, transformed into another phase, alloyed or any combination thereof, to produce the components or the entirety of the optical or medical sensor device disclosed herein.

As used herein, the term "titania" refers to any phase of the titanium-oxygen system. The chemical composition of the Ti—O system may be referred to as $Ti_nO_{2n-1}$ or otherwise $TiO_x$ where x is a rational number that can vary from essentially zero (0) to two (2). The term titania also refers to any phase of the Ti—O system, for example being rutile, anatase, brookite, honquiite or any combination thereof.

As used herein, the term "web" refers to the nanofibrous network that is self-supported in 2D or 3D, the web can have varying degrees of porosity which is determined by the nanofiber coordination and linking. The webs are connected to some extent throughout all directions.

As used herein, the term "vias" means a feature with a low ratio of surface area affected by material removal to the overall surface area and where the feature has an approximately equal surface aspect ratio. The depth of the vias may be through the partial material thickness (i.e. blind vias) or through the entire material thickness (i.e. through vias).

The nanofibers, previously defined in this disclosure as being NP strands, have been successfully synthesized on titanium substrates, are very surprisingly disclosed herein demonstrated herein as being useful SERS sensors.

A component of the sensors disclosed herein involves the micro-pattern features which are developed simultaneously with the nano-structures. The micro features may be vias, open channels, enclosed channels, junctions, locally oxidized surfaces or any combination thereof (for example, see Jariwala et al.). These micro-patterns may be completely or partially covered by the nanostructures. In either case, coverage implies that it may still be possible to interact with the underlying material below the top layer of the 3D nanofiber network by non-limiting means such as inherent porosity, optical transparency, hybridization etc. The micro-pattern features add partial functionality to the optical sensor device and allow the skilled artisan of the device to have a greater degree of flexibility when tailoring the sensor towards specific applications.

A. Synthesis and Usage Procedure

To this date, there are insufficient characterization and testing tools available to fully specify the features of the 3D nano-fibrous network. A complementary manufacturing method will be described instead which discloses the best known practice to develop the present optical sensor.

A femtosecond laser with diode-pumping, mode-locking, and Yb-doped fiber amplification (Clark-MXR IMPULSE™ Series) may be used to generate the titania nano-fibers from a commercially pure titanium substrate (Ti ca. 98.9% purity). The central laser wavelength (generated second harmonic at 515 nm), power (16 W), pulse duration (214 fs), polarization (circular), and piezo scanning speed (1000 μm/s) are preferably kept constant under single pulse irradiation. Prior to irradiation, a dot-array pattern is preferably plotted with computer-aided design (CAD) software such as EzCAD©. Once galvanometer scanning is initiated, the acousto-optical modulator blocks the irradiation between successive points for the dot-array pattern.

As an alternative to single event laser pulse irradiation, subsequent irradiation events may be desirable to control the NP average diameters and size distribution of the nano-fiber network. The purpose of controlling the NP average diameter and size distribution would be appreciated by a skilled artisan in the field of optical and medical devices that use optical sensor principals (e.g. control NP aggregation, modify NP surface energy, NP phase transformation etc.). Furthermore, synthesis optimization may be performed under partial vacuum up to ambient atmosphere conditions.

Given the flexibility of the manufacturing method and the versatility of possible sensor materials, glass and laboratory glass surfaces may likewise be modified for Raman sensing applications. As a non-limiting example, the pulsed laser may be focused onto the inner surface of a transparent vial for direct nano architecture synthesis. This provides the advantage of easy integration into laboratory standard practices and further expands the application potentials of Raman spectroscopy.

A characterization technique is also developed to better assist in the optimization process. The technique is based on scanning near-field optical microscopy (SNOM). SNOM is used to collect reflection data across one micro-via. The micro-via may be fully or partially covered by the nanofibrous network depending on the synthesis parameters. A normalized roughness construct is developed as $G=Sa-Sa/Max$, where Sa (V) is the average roughness and Max (V) is the maximum roughness. The goal is to target the G value to be included in the range of functioning sensors for particular analyte conditions. As a result, a device can be analyzed for quality assurance with the disclosed G criteria to predict the optical sensing performance.

The optical sensor is developed for micro-Raman analysis and to function with the following set of parameters:
1. the analyte is exposed to the sensor surface;
2. if desirable, the analyte may be dried prior to micro-Raman analysis;
3. if desirable, Raman reporter molecules may be used at any point or the experimentation or analysis;
4. if desirable, a transparent and low fluorescence glass may be used to cover the top surface, in essence sandwiching the analyte between the sensor surface.
5. the sensor now together with the applied analyte are placed perpendicular to the laser beam for Raman spectroscopy;
6. the area desired for analysis is positioned by translation to be directly irradiated by the laser beam for Raman spectroscopy;
7. if desirable, a handheld Raman unit or fiber optic probe may be positioned in a similar manner to the sample as opposed to positioning the sample to the laser beam;
8. the support holding the sensor under the laser may be stationary;
9. the support holding the sensor under the laser may be translating, rotating, or any combination thereof;
10. the support holding the sensor under the laser preferably has minimum surface vibration;
11. the sensor is preferably exposed to room temperature during experimentation or analysis;
12. the sensor is preferably exposed to room pressure during experimentation or analysis;
13. the sensor is preferably exposed to minimum ambient light during experimentation or analysis;
14. the sensor is preferably exposed to minimum atmospheric convection during experimentation or analysis;
15. the sensor is preferably exposed to minimum acoustic noise levels during experimentation or analysis;
16. all Raman data collection is preferably performed consecutively, with minimum down time between acquisitions; and
17. the acquired Raman data may be analyzed in space, time, or any combination thereof.

B. Description of Exemplary Embodiments

Figure 3:
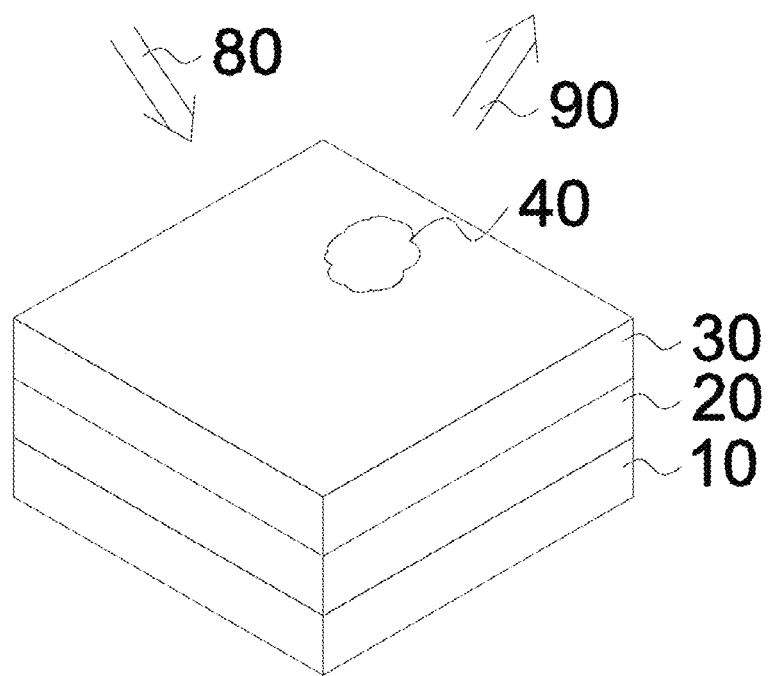
FIG. 3 is a non-limiting possibility of the physical layout of one optical sensor pad; the number of sensor pads on the substrate surface may vary from one to a plurality thereof and may not necessarily have a square section nor all be uniform.

In an embodiment, the device is used as an optical sensor for detection of analytes to which the sensor is exposed. This enables laboratory, manufacturing, and field environment analysis subject to suitable Raman equipment availability. The general schematic diagram of the use of the present sensor is illustrated in FIG. 3 which shows a number of sensor pads on the substrate surface may vary from one to a plurality thereof and may not necessarily have a square section nor all be uniform. More particularly the sensor pad is formed on the surface of a titanium substrate 10, with micro features 20 formed on the surface and nano features 30, specifically nanofibers formed over and around the micro features. As a sensor an analyte 40 is bound to the sensor pad and incident radiation 80 is incident on the pad and scattered radiation 90 is detected and analyzed.

This approach can be used in analytical scenarios such as volatile organic compounds (VOCs), in groundwater samples or hydrocarbon mixtures in petroleum refinery or recovery. The uses of device disclosed herein includes, but are not limited to: environmental monitoring, genomics and proteomics research, DNA analysis, pharmaceutical industry, drug industry, agriculture and food analysis, biomedical diagnosis, bio-defence, industrial monitoring, forensic analysis etc.

Nanofibers

One aspect of this disclosure is the the 3D self-supported nanofiber structure made from titanium. The nanofibers are composed of generally spherical NPs that interact in a manner as to arrange themselves into essentially single-strand or multi-strand components that form a multiplicity of porous web-like features having the capability of supporting themselves in a 3D architecture. The interactions and arrangements of the sensor occur usually without chemical additions or reagents but rather are induced by the laser ablation plasma dynamics. When submerged into a liquid solution, it is found that the nanofiber matrix has some degree of solubility. The titania and fiber matrix is found to be partially dissolved, displaced or any combination thereof, in simulated body fluid (SBF) solutions. In the SBF solutions, some of the nanofiber matrix remained underneath the hydroxyapatite precipitation yet some may have been embedded into the SBF deposits (for example, reference Tavangar et al.). In all of the cases, the solubility, displacement or combination thereof, properties of the nanofiber network suggest that the 3D nanofiber network actively interacts with the applied analyte.

In some embodiments, the nano-fibers may be optionally combined with plasmonic materials to further enhance the optical sensing capabilities. This combination may be in the form of a film coating, NP coating, alloying, sintering, structural combination or any combination thereof.

System Component

In some embodiments, the sensor may be incorporated into a larger system. For example, the substrate may be incorporated into a micro-electro-mechanical system (MEMS). MEMS are integrated systems comprising mechanical elements, sensors, actuators, and electronics. All of those components may be manufactured by known microfabrication techniques on a common chip, comprising a silicon-based or equivalent substrate (e.g. PolyMUMPS). The sensor components of MEMS may be used to measure mechanical, thermal, biological, chemical, optical, magnetic or any combination thereof, phenomena. The electronics may utilize the information from the sensors and control actuator components such pumps, valves, lasers, ultrasonic devices, magnetic resonance devices, dialysis devices, heaters, coolers, filters, etc.

In some embodiments, the sensor surface may deliver certain nanostructured material, drugs, hormones, molecular species or a combination thereof when the sensor is activated. The sensor disclosed herein may act as a component in a monitoring device that functions as a closed-loop system for molecular delivery and health monitoring.

Non-Limiting Example of Nano Fiber Sensor Development for Titania

In some embodiments, the broad laser processing parameters to producing the titania based SERs sensors are as follows: the laser wavelength may be varied in a range from about 532 to about 1064 nm, the laser pulse intensity may be varied in a range from about $10^6$ to about $10^{14}$ W/cm$^2$, the pulse repetition rate may be varied in a range from about 4 to about 26 MHz, the irradiation time may be varied in a range from about 0.1 to about 25 msec, and the pulse duration may be varied in a range from about 100 fs to about 10 ps.

In other embodiments the wavelength may be in a range of the fundamental modes from about 790 to about 1100 nm and including their second and third harmonics, and wherein the laser pulse intensity is in a range from about $10^6$ to about $10^{14}$ W/cm$^2$, and wherein the pulse repetition rate is in a range from about 1 to 90 MHz, and wherein the effective irradiation time is in a range from about 0.1 to about 25 msec, and wherein pulse duration is in a range from about 100 fs to about 10 ps.

FIG. 1 shows a scanning electron microscopy (SEM) image of the 3D titania nanofibrous network with this particular network shown is generated at a wavelength of 1040 nm, repetition rate of 13 MHz and an irradiation time of 20 msec (i.e. from about 13 MHz and 20 msec), pulse intensity of $1.1 \times 10^{13}$ W/cm$^2$, and a pulse duration of 214 fs. Other variations of laser repetition rate and irradiation time yield similar SEM images, with variations in nanofibrous porosity, 3D network depth and the total effect on the substrate (e.g. depth of the micro-vias, micro-via rim height etc.).

Figure 2:
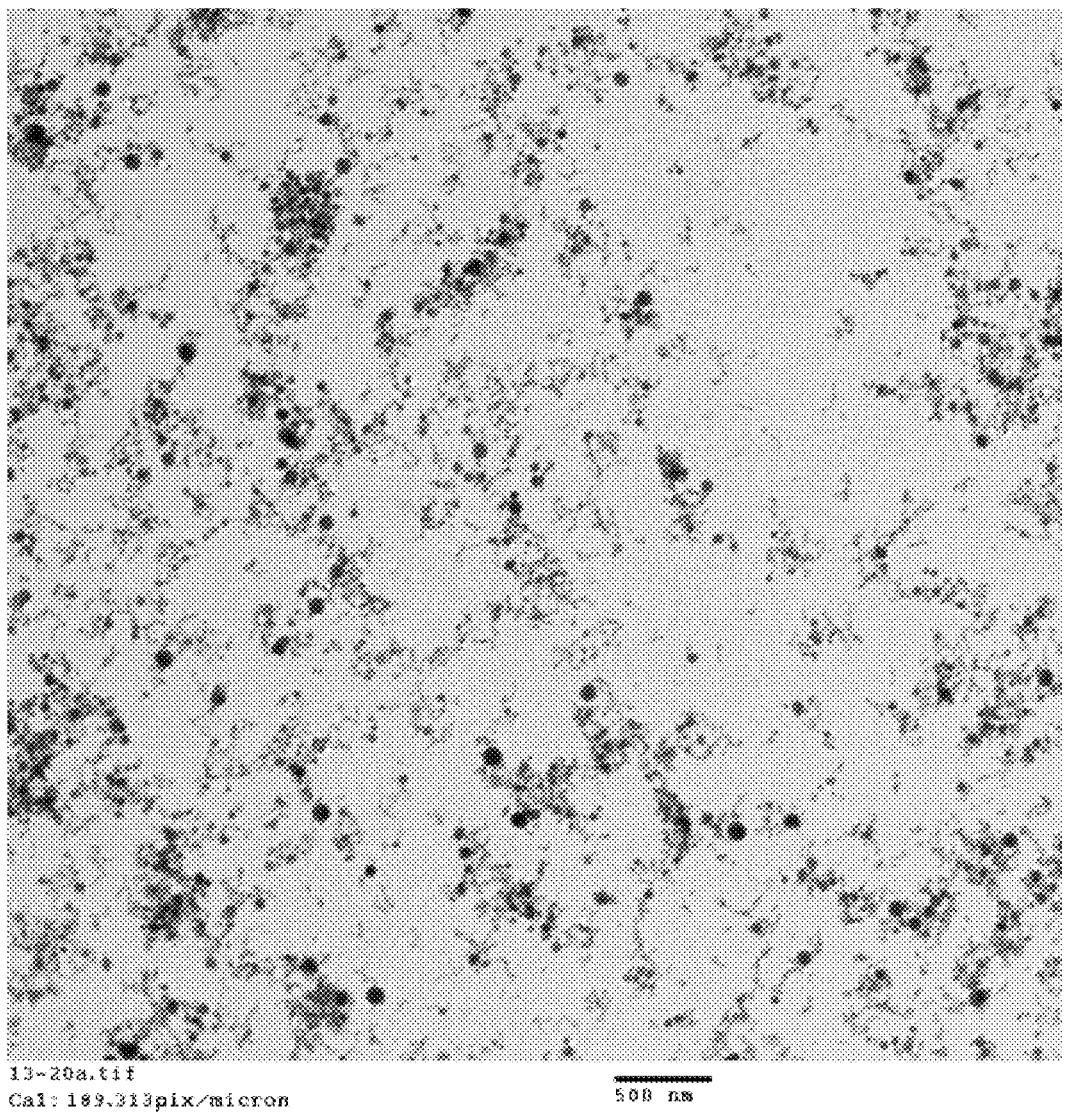
FIG. 2 is a transmission electron microscopy (TEM) image of the partial 3D titania nanofibrous network that is transferred by electrostatic interactions to a TEM grid; the particular network shown is generated at a laser pulse repetition rate of 4 MHz and an irradiation time of 1 msec with subsequent irradiation at 26 MHz and 10 msec; other variations of laser repetition rate, irradiation time, and subsequent irradiation processing steps yield similar TEM images, with variations in nanofibrous aggregation, individual NP size distribution, and length of the nanofiber segments.

FIG. 2 is a transmission electron microscopy (TEM) image of the partial 3D titania nanofibrous network that is transferred by electrostatic interactions to a TEM grid; the particular network shown is generated with the same parameters as with FIG. 1, except varying the pulse repetition rate and irradiation time as well as adding a subsequent irradiation event to increase the distribution of nanoparticle diameter sizes. The repetition rate and irradiation time were first set to 4 MHz and 1 msec respectively and the subsequent irradiation event was set to 26 MHz and 10 msec respectively. Other variations of laser repetition rate, irradiation time, and subsequent irradiation processing steps yield similar TEM images, with variations in nanofibrous aggregation, individual NP size distribution, and length of the nanofiber segments.

The nanofibers are typically found to arrange into porous web structures such as shown in FIG. 1. These pores are on average 750-850 nm and increase with a reducing laser pulse repetition rate. When the nanofibers are partially removed from the 3D network by a TEM grid, the nanofibers tend to maintain their NP to NP coordination as evidenced from TEM images (FIG. 2). Also witnessed from TEM images is that the individual NPs can have multiple titania phases. TEM images also reveal that these individual NPs may sometimes sinter into a single NP or into a nanowire.

The produced nanofibers are found to be generally flexible and mobile. For example, the nano-fiber matrix is found to be highly elastic over a large range of forces with atomic force microscopy (AFM). The nano-fibrous matrix may be penetrated by the AFM scanning tip in contact mode and it is possible for the scan to continue without significant interference from the AFM probe. Under dense and thick nano-fiber network conditions, however, significant interference during the scan is noticed as the scanning signal saturates and noise dominates the image. This is determined to be an effect of variable mechanical properties of the 3D nano-fibrous matrix by varying the synthesis parameters.

Referring to the electron microscopy images of titania nano-fibers of FIGS. 1 and 2, the individual titania NPs can range in size from several hundred nm down to several nm. The most average NP size is found to be in the range of 20-30 nm and increasing with lower laser pulse repetition rates. The NPs are also essentially spherical when considered individually. The X-ray diffraction (EDX) patterns indicate that the NPs are generally crystalline. When analyzed by EDX at the synthesis parameters at a repetition rate of 13 MHz and an irradiation time of 20 msec, the O atomic weight is determined to be approximately 74% and the Ti atomic weight is determined to be approximately 26%. Other variations of laser repetition and irradiation time result in approximately 6% deviations in Ti and O atomic weights.

In order to control the NP average diameter and size distribution, the laser irradiation time may be increased from 1 msec to 10 msec. This may reduce the average NP size from essentially 90-105 nm to essentially 40-50 nm. As another example, it may be desirable to reduce the laser pulse repetition rate from 26 MHz to 13 MHz to narrow the NP size distribution or the average size deviation. For titania nano fibers, this may reduce the standard deviation by essentially 10 nm. This preceding synthesis control example is universal by material and varies only quantitatively by magnitude. Controlling the nanofiber crystal structure and composition may be necessary to further control the analyte dynamics at the disclosed sensor surface. By reducing the pulse repetition rate from 26 MHz to 4 MHz, a gradual increase in the amount of anatase titania content was observed. In some optical sensor designs, a greater anatase phase composition may be more favorable for photocatalytic and surface energy features. Moreover, an increase in laser irradiation time from about 10 msec to about 25 msec has been observed to increase the amount of Ti amorphous content. To reduce the degree of oxidation, an increase in pulse duration from about 214 fs to the ps regime may be desirable. A clear indication of reduced titania oxidation is a shift from a white colored pigment to a blue colored pigment.

To optimize the 3D nanofibrous titania sensor that can be reproduced by this disclosure, it may be necessary to adjust the parameters in the following manner: vary the irradiation time from about 0.1 msec to about 25 msec and vary the laser pulse repetition rate from about 4 MHz to about 26 MHz. Naturally, this method of varying the combination of laser irradiation time and repetition rate may result in an array sensor product (plurality of sensor pads shown in FIG. 3). In terms of the MHz-msec synthesis parameters (i.e. laser pulse repetition rate and irradiation time), the array sensor may have all, selected or single combinations in some pattern on the surface. For example, the surface may have square patches of the nanostructured titania material of a certain dimension and certain separations. For synthesized square patches: 1-2 mm was found to be a minimum separation to reduce nanofiber overlapping, a separation up to 5 mm is a minimum to contain the analyte droplet from wetting other adjacent patches/sensor pads. For individual micro-vias: the separation criteria depends on the laser intensity (e.g. repetition rate affecting material heating) and pulse duration (e.g. reduced duration reduces the plasma width and increase its height). As a result, higher intensity and longer pulse duration can accommodate larger spacing for nanofibrous network generation. The discovered rule of thumb for the range of parameters disclosed herein is to separate the vias by their diameter.

For the titania 3D nanofibrous optical sensor, the synthesis irradiation time increment is 5 msec. As well, the preferred pulse repetition rates for the synthesis of the optical sensor may be 4, 8, 13, and 26 MHz noting that these are the equipment limited repetition rates, and any frequency in the range from about 4 to about 26 MHz will work. Synthesis may be performed under ambient atmosphere conditions or partial vacuum or conditions between these two.

Figure 4:
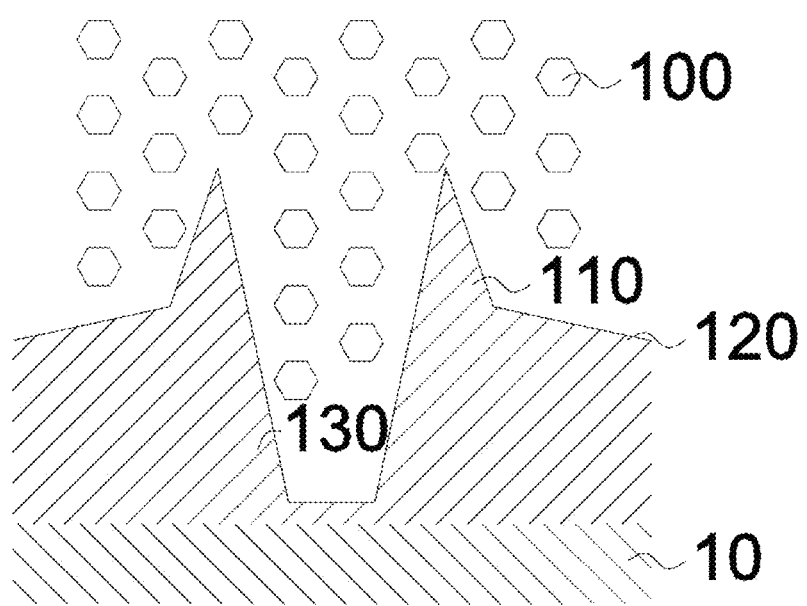
FIG. 4 is a non-limiting example of the cross section of the structure of FIG. 3 showing a titanium substrate with micro features produced therein and nanostructures formed of nanofibers formed on top of the micro features in which the nanostructure is shown to be self-supporting in all three rectangular coordinate dimensions, and the nanofibers may also lay flat on top of the base sensor surface and are also not necessarily separated uniformly and tend to arrange in a web-like form as evidenced from the SEM of FIG. 1.

FIG. 4 shows a titanium substrate 10 having a micro surface pattern 110 formed therein by the laser processing discussed above, and a nanowire web structure 100 formed over and around the micro surface pattern 110. The micro surface pattern 110 may have features 130 below the sensor base surface 120.

Figure 5:
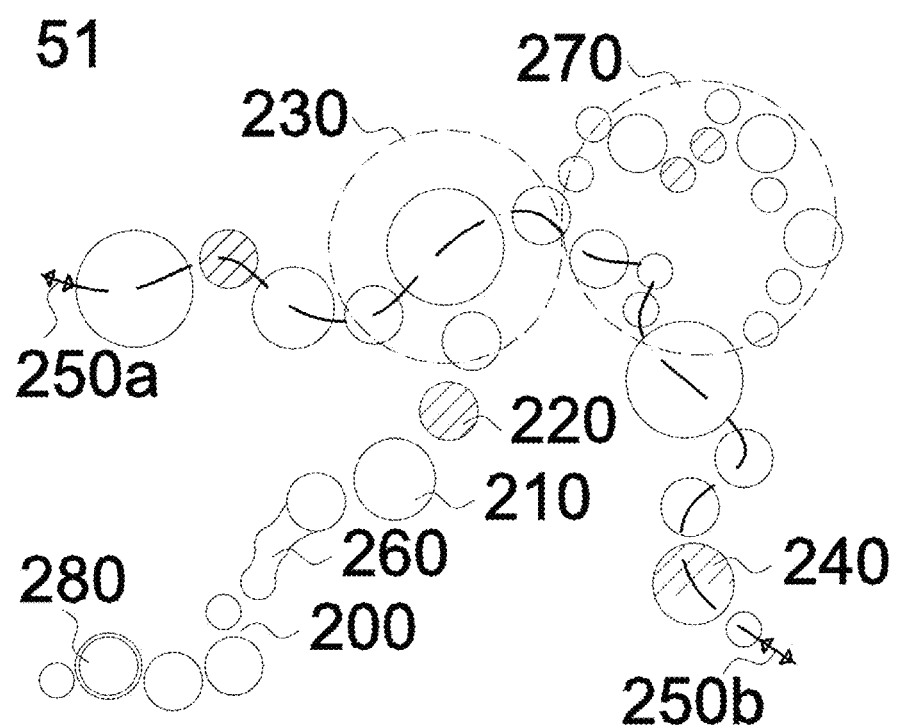
FIG. 5 is a diagrammatic representation of a non-limiting example of a nanofiber; the composition and morphology of the nanofiber depends on the synthesis parameters and experimental conditions as disclosed in this disclosure; the nanofiber structure may have all of the features or a selection of more dominant features; some illustrated nanofiber features may be identified from the titania nanofiber TEM image of FIG. 2.

FIG. 5 is a diagrammatic representation showing a non-limiting example of a web structure 100 formed by nanofiber 51. As noted above, the composition and morphology of the nanofiber depends on the synthesis parameters and experimental conditions. In the nanofiber some of the nanoparticles (NPs) may be rutile NPs 210, and others may be anatase NPs 220, and still others may be an alloy 240 of rutile and anatase.

Some of the NPs in the nanofiber 51 may be separated by a nanogap 200 but are still aligned with their neighbors by the weak forces discussed above. Some of the NPs 260 may be sintered together (i.e., being held together by strong forces such that several NPs are sintered to form a nanowire. Some of the NPs 280 may be oxidized, coated, contaminated or a combination thereof. Sections of the nanowire that are branching are shown at 230, and a looped section forming part of the web structure is shown at 270. The ability of the nanofiber to stretch and compress in reaction to force is diagrammatically illustrated by the two nodes 250a and 250b. Nodes 250a and 250b are essentially nodes that stretch apart or approach each other to provide an impression of nanofiber stretching/compressing. Such stretching has been experimentally observed by the inventors.

There may be one or more statistical distributions of the size of the NPs. For example, considering the NP diameter distribution of about 5 to about 150 nm, there may be a lognormal distribution for NPs on the lower range and another lognormal distribution for NPs on the higher range. This may be related to the presence of two titania phases, e.g. anatase and rutile, but we have yet to confirm with certainty (results not published). Simply said, there is a statistical distribution of nanofiber NP diameters as opposed to a single diameter chosen from about 5 to about 150 nm.

Analyte Sensor Examples

This disclosed procedure of varying the laser pulse repetition rates and dwell times is used in demonstrating the practicality of using the sensor as a sensor for bisphenol-A (BPA), diclofenac sodium salt (DCFNa) BPA and DCFNa, non-limiting examples chosen due to their characterization as common water pollutants. For BPA, a useful set of laser synthesis parameters for a 3D titania nanofibrous optical device is setting the repetition rate and irradiation time combinations to about 13 MHz and 20 msec respectively (dry residue) and 4 MHz and 1 msec respectively (aqueous) while keeping the laser wavelength at 1040 nm, and pulse duration at 214 fs. For DCFNa, the optimum set of synthesis parameters for a 3D titania nanofibrous optical sensor is about 8 MHz and 15 msec (dry residue) and no clear optimum for aqueous. By generalizing the results from BPA and DCFNa, the repetition rate (MHz) and irradiation time (msec) synthesis parameters with the best analyte detection include essentially 8-1, 8-15, 13-15, 13-20, and 26-10 (MHz-msec). Based on average performance, the 13 MHz and 15 msec synthesis parameter supports the smallest standard deviation while the 13 MHz and 20 msec synthesis parameter supports the largest standard deviation of Raman sensor performance.

The G normalized roughness construct described in this disclosure may be used to test and assure the quality of the synthesized titania sensor. The array of synthesis parameters range from essentially 4 MHz and 1 msec to essentially 26 MHz and 25 msec, inclusively as previously described in this section while keeping the laser wavelength at 1040 nm, and pulse duration at 214 fs. A normalized roughness construct is developed as G=Sa−Sa/Max, where Sa (V) is the average roughness and Max (V) is the maximum roughness. The G=−0.0021 to +0.0411 criteria is found to correspond to functioning optical sensors for BPA and DCFNa. As a result, a device can be analyzed with the disclosed G criteria to predict the optical sensing performance.

Optionally, it is also found that these nanofibers may be coated with a dye such as rhodamine 6g (R6G) or crystal violet (CV) to enhance the detection capability of the analyte. An effective method of coating the nanofiber network is found to be first applying a drop of the dye over top of the nanofibrous network and subsequently drying the dye with a laser. Effective laser specifications are found to include a continuous laser beam in the visible wavelength (e.g. 514 nm), laser power between 1 mW and 100 mW, laser focus spot size of 5-10 μm and an irradiation time of up to one minute. The skilled artisan will realize that the methods and apparatus are not limiting as to the type of analysis that may be performed, but rather that the methods and apparatus suggest an effective method for the detection, identification, quantification or any combination thereof of aromatic environmental pollutants such as BPA and DCFNa.

Optical Sensor Method

Incident electromagnetic energy, preferably a visible (VIS) or otherwise an ultra-violet (UV) or an infrared (IR) laser, is focused onto the sensor. The power of the incident energy used to irradiate the analyte is typically below the analyte's damage threshold. This threshold may vary from $W/cm^2$ to $kW/cm^2$ depending on the analyte and the specific experimental conditions. A power density higher than the analyte's damage threshold may be desired for applications including but not limited to, analyzing molecular reaction dynamics, catalysis, photo-initiation, laser ablation, charge transfer, degradation, physical phase transformation, crystallographic phase transformation, resin curing, cellular uptake, cellular damage etc. The generated Raman signal of the analyte, substrate or a combination thereof, is essentially detected and transmitted to a computer for the purposes of analyte detection, identification, quantification or any combination thereof. A non-limiting example of a Raman detection unit is disclosed by U.S. Pat. No. 6,002,471 which is incorporated herein in its entirety by reference.

In another embodiment, a portable version of the Raman spectrometer may be used. As a non-limiting example, the portable version may be in the form of a hand-held device as offered by Ocean Optics, Florida (U.S.). The Raman system may also use hyperspectral spectrometer principles that can offer instantaneous spatial information of the sensor surface. In this case, the acquired information may be compared immediately between spatially separated points of interest. As a non-limiting example, the Raman hyperspectral spectrometer may be in the form provided by P&P Optica, Ontario (Canada) or by Photon etc., Quebec (Canada). In the aforementioned embodiments, a variety of laser wavelengths may be used in sequence or simultaneously during various experimental stages. Pulsed laser beams, continuous laser beams, or a combination thereof may be used.

In another embodiment, the optical sensor is readily suitable for other optical sensor methods known in the art such as normal Raman scattering, Raman microprobe, confocal Raman microspectrometry, UV-Raman microscopy, surface-enhanced Raman scattering (SERS), surface enhanced resonance Raman spectroscopy (SERRS), tip-enhanced Raman spectroscopy (TERS), hyper-Raman, coherent anti-Stokes Raman spectroscopy (CARS), stimulated Raman scattering, inverse Raman spectroscopy, stimulated gain Raman spectroscopy, three-dimensional Raman, or any combination thereof.

An embodiment of a titanium based Surface Enhance Raman Scattering (SERS) system comprises a sensor including a titanium substrate having a surface and an array of sensor locations located in a predefined portion of the surface, with each of the sensor locations including a micro-pattern feature in the surface of the substrate and nanofibers that generally surround and envelop the micro-pattern feature. The nanofibers are comprised of a plurality of titanium based nanoparticles aligned into a self-supported web structure, with the array of sensor locations exhibiting SERS activity. The system includes a sample cell for receiving the sensor with the sample cell being configured to allow exposure of the sensor to a fluid being tested for the presence of an analyte. A laser source is positioned for illuminating the array of sensor locations with laser light and a detector is positioned for detecting laser light scattered from the sensor post exposure of the sensor to the fluid.

Generally computer control for determining the presence of the analyte would not be necessary because the user/operator can usually tell the presence of the analyte by judging the spectrum. However an operator may need assistance interpreting the spectrum if the spectrum is something new to the user/operator. Thus, optionally a computer processor may be included which is programmed to match the detected spectrum of the scattered light to a spectral library of analytes.

In some embodiments, the analytes may be partially or fully Raman labeled. In other embodiments, the nanostructured surface may be Raman labeled. The Raman labels may be subsequently irradiated to promote curing, drying, diffusion, mixing, or a combination thereof. The skilled artisan will realize that the methods and apparatus are not limiting as to the type of analytes that may be detected, identified, quantified or any combination thereof.

Optical Sensor Method Extension to Field Applications

In some embodiments, the sensor surface may be exposed to the analyte by direct contact with the region of interest. As a non-limiting example, one may press the sensor surface against an unknown powder of any orientation and subsequently use the said sensor for Raman analysis. In another example, the material may be essentially transparent to the laser beam. In this case, the sensor surface may be pressed against the unknown powder and the laser beam may provide excitation for the Raman scattered energy from the backside of the sensor surface. In essence, the surface would not be relieved from the region it contacted and the Raman spectrum may be collected immediately, preferably by a portable Raman system. A non-limiting example of this portable Raman system is offered by Ocean Optics, Florida (U.S.).

The said examples for the determination of unknown powders may also be extended to liquid and gaseous analysis. A non-limiting case includes a container with an interior geometry that acts to contain the liquid or gas. The interior geometry will have a single or a plurality of developed sensor surfaces. The container is transparent to the laser beam which may be a form of glass or quartz. The container is then irradiated by the laser beam from the exterior to reach the interior area with the developed sensor surface. Subsequently, the Raman scattered energy is collected back from the interior and registered by the portable Raman system. In case of the container being a vial, such a portable Raman system is currently offered by Ocean Optics, Florida (U.S.). The aforementioned portable Raman system extensions are not exclusive to field applications and may readily be adapted for a laboratory or manufacturing environment.

As used herein, the terms, "comprises" and "comprising" are to be construed as being inclusive and open ended, and not exclusive. Specifically, when used in this specification including claims, the terms, "comprises" and "comprising" and variations thereof mean the specified features, steps or components are included. These terms are not to be interpreted to exclude the presence of other features, steps or components.

The foregoing description of embodiments of the sensor disclosed herein has been presented to illustrate the principles of the invention and not to limit the invention to the particular embodiment illustrated. It is intended that the scope of the invention be defined by all of the embodiments encompassed within the following claims and their equivalents.

REFERENCES CITED

Canadian Patent Documents

| 2566123 | May 2005 | Poponin |
| 2611985 | June 2006 | Joseph et al. |

U.S. Patent Documents

| 5,580,655 | December 1996 | El-Shall et al. |
| 20050018274 | January 2005 | Halas et al. |
| 6,778,316 | August 2004 | Halas et al. |
| 20050221072 | October 2005 | Dubrow et al. |
| 20050038498 | February 2005 | Dubrow et al. |
| 7,385,691 | June 2008 | Islam et al. |
| 20030231304 | December 2003 | Chan et al. |
| 6,970,239 | November 2005 | Chan et al. |
| 7,400,395 | July 2008 | Chan et al. |
| 6,002,471 | December 1999 | Quake |

Other References

Musumeci, A. et al., "SERS of Semiconducting Nanoparticles (TiO2 Hybrid Composites)," J. Am. Chem. Soc. (2009) 131: 6040-6041.

Tan, B. et al., "Synthesis of Fibrous Nanoparticle Aggregates by Femtosecond Laser Ablation in Air," Opt. Express (2009) 17: 1064-1069.

Jariwala, S. et al., "Micro-Fluidic Channel Fabrication via Two-Photon Absorption (TPA) Polymerization Assisted Ablation," J. Micromech. Microeng. (2009) 19: 115023_1-115023_6.

Sivayoganathan, M. et al., "Effect of Mega-Hertz Repetition Rate on the Agglomerated Particle Size of Femtosecond Synthesized Nanostructures," Opt. Mater. Express (2012) 2: 987-995.

Maznichenko et al., "TiO$_2$Nanofibrous Interface Development for Raman Detection of Environmental Pollutants," App. Phys. Lett. (2012) 101: 231602_1-231602_5.

Tavangar et al., "Synthesis of Bio-Functionalized Three-Dimensional TitaniaNanofibrous Structures Using Femtosecond Laser Ablation," ActaBiomater. (2011) 7: 2726-2732.

The invention claimed is:

1. A method of producing a titanium based Surface Enhance Raman Scattering (SERS) sensor, comprising:
providing a titanium substrate having a surface and producing an array of sensor locations in a predefined portion of the surface by irradiating the predefined portion of the surface in the presence of air with laser pulses having an intensity, a wavelength, a pulse duration, an effective irradiation time and a pulse repetition rate selected to produce, at each sensor location, a micro-pattern feature in the surface of the substrate and a self-supported web structure that generally surround and envelop the micro-pattern feature, said self-supported web structured being made of nanofibers each comprised of a plurality of titanium based nanoparticles aligned into said self-supported web structure, wherein said array of sensor locations exhibit SERS activity.

2. The method according to claim 1 wherein the wavelength is in a range from about 532 to about 1064 nm, and wherein the laser pulse intensity is in a range from about $10^6$ to about $10^{14}$ W/cm$^2$, and wherein the pulse repetition rate is in a range from about 4 to about 26 MHz, and wherein the effective irradiation time is in a range from about 0.1 to about 25 msec, and wherein pulse duration is in a range from about 100 fs to about 10 ps.

3. The method according to claim 1 wherein the wavelength is in a range of the fundamental modes from about 790 to about 1100 nm and including their second and third harmonics, and wherein the laser pulse intensity is in a range from about $10^6$ to about $10^{14}$ W/cm$^2$, and wherein the pulse repetition rate is in a range from about 1 to 90 MHz, and wherein the effective irradiation time is in a range from about 0.1 to about 25 msec, and wherein pulse duration is in a range from about 100 fs to about 10 ps.

4. The method according to claim 1 wherein said titanium based nanofibers are structured by alignment of individual titanium based nanoparticles, wherein in each titanium based nanofiber said individual titanium based nanoparticles are held together by one or both of
strong forces such that neighboring titanium based nanoparticles are physically joined together,
weak forces such that neighboring titanium based nanoparticles are spaced apart up to about 1 nm but are aligned in said titanium based nanofiber.

5. The method according to claim 1 wherein said micro-pattern feature is in the form of any one or combination of vias, open channels, enclosed channels, junctions, and locally oxidized surfaces.

6. A Raman spectroscopy based method of detecting an analyte, comprising the steps of:
a) providing a titanium substrate having a surface and producing thereon a sensor including an array of sensor locations in a predefined portion of the surface by irradiating the predefined portion of the surface with laser pulses having an intensity, a wavelength, a pulse duration, an effective irradiation time and a pulse repetition rate selected to produce, at each sensor location, a micro-pattern feature in the surface of the substrate and titanium based nanofibers that generally surround and envelop the micro-pattern feature, said nanofibers being comprised of a plurality of titanium based nanoparticles aligned into a self-supported web structure, wherein said array of sensor locations exhibit SERS activity; and
b) exposing said sensor to a sample being tested for the presence of said analyte and thereafter recording a Raman spectra after irradiating the analyte sensor with a laser beam and correlating said Raman spectra to a characteristic Raman spectra of the analyte to determine the presence or absence of the analyte in the sample.

7. The method according to claim 6 wherein the wavelength is in a range of the fundamental modes from about 790 to about 1100 nm and including their second and third harmonics, and wherein the laser pulse intensity is in a range from about $10^6$ to about $10^{14}$ W/cm$^2$, and wherein the pulse repetition rate is in a range from about 1 to 90 MHz, and wherein the effective irradiation time is in a range from about 0.1 to about 25 msec, and wherein pulse duration is in a range from about 100 fs to about 10 ps.

8. The method according to claim 6 wherein the wavelength is in a range of the fundamental modes from about 790 to about 1100 nm and including their second and third harmonics, and wherein the laser pulse intensity is in a range from about $10^6$ to about $10^{14}$ W/cm$^2$, and wherein the pulse repetition rate is in a range from about 1 to 90 MHz, and wherein the effective irradiation time is in a range from about 0.1 to about 25 msec, and wherein pulse duration is in a range from about 100 fs to about 10 ps.

9. The method according to claim 6 wherein said titanium based nanofibers are structured by alignment of individual titanium based nanoparticles, wherein in each titanium based nanofiber said individual titanium based nanoparticles are held together by one or both of
strong forces such that neighboring titanium based nanoparticles are physically joined together,
weak forces such that neighboring titanium based nanoparticles are spaced apart up to about 1 nm but are aligned in said titanium based nanofiber.

10. The method according to claim 9 wherein said titanium based nanofiber nanoparticles are in the form of any one or combination of anatase, rutile, and amorphous titania phases with generally spherical morphology in a size range from about 5 to about 150 nm.

11. The method according to claim 6 wherein said micro-pattern feature is in the form of any one or combination of vias, open channels, enclosed channels, junctions, and locally oxidized surfaces.

12. The method according to claim 6 wherein the Raman spectroscopy based method of detecting an analyte uses in step b) any one or combination of Raman scattering, Raman microprobe, confocal Raman microspectrometry, UV-Raman microscopy, surface-enhanced Raman scattering (SERS), surface enhanced resonance Raman spectroscopy (SERRS), tip-enhanced Raman spectroscopy (TERS), hyper-Raman, coherent anti-Stokes Raman spectroscopy (CARS), stimulated Raman scattering, inverse Raman spectroscopy, stimulated gain Raman spectroscopy, three-dimensional Raman spectroscopy, and hyperspectral Raman spectroscopy.

13. A titanium based Surface Enhance Raman Scattering (SERS) sensor, comprising:
a titanium substrate having a surface and an array of sensor locations located in a predefined portion of the surface, each of said sensor locations including a micro-pattern feature in the surface of the substrate and nanofibers that generally surround and envelop the micro-pattern feature, said nanofibers being comprised of a plurality of titanium based nanoparticles aligned into a self-supported web structure, wherein said array of sensor locations exhibit SERS activity.

14. The method according to claim 13 wherein said titanium based nanofibers are structured by alignment of individual titanium based nanoparticles, wherein in each titanium based nanofiber said individual titanium based nanoparticles are held together by one or both of
strong forces such that neighboring titanium based nanoparticles are physically joined together,
weak forces such that neighboring titanium based nanoparticles are spaced apart up to about 1 nm but are aligned in said titanium based nanofiber.

15. The method according to claim 13 wherein said titanium based nanofiber nanoparticles are in the form of any one or combination of anatase, rutile, and amorphous titania phases with generally spherical morphology in a size range from about 5 to about 150 nm.

16. A titanium based Surface Enhance Raman Scattering (SERS) system, comprising:
a) a sensor including a titanium substrate having a surface and an array of sensor locations located in a predefined portion of the surface, each of said sensor locations including a micro-pattern feature in the surface of the substrate and nanofibers that generally surround and envelop the micro-pattern feature, said nanofibers being comprised of a plurality of titanium based nanoparticles aligned into a self-supported web structure, wherein said array of sensor locations exhibit SERS activity;
b) a sample cell for receiving said sensor, said sample cell being configured to allow exposure of said sensor to a fluid being tested for the presence of an analyte;
c) a laser source for illuminating said array of sensor locations with laser light; and d) a detector for detecting laser light scattered from said sensor post exposure of said sensor to said fluid.

17. The system according to claim 16 including a computer processor connected to said detector and programmed to match the detected spectrum of the said scattered light to a spectral library of analytes.

18. The system according to claim 16 wherein said titanium based nanofibers are structured by alignment of individual titanium based nanoparticles, wherein in each titanium based nanofiber said individual titanium based nanoparticles are held together by one or both of
- strong forces such that neighboring titanium based nanoparticles are physically joined together,
- weak forces such that neighboring titanium based nanoparticles are spaced apart up to about 1 nm but are aligned in said titanium based nanofiber.

19. The system according to claim 16 wherein said titanium based nanofiber nanoparticles are in the form of any one or combination of anatase, rutile, and amorphous titania phases with generally spherical morphology in a size range from about 5 to about 150 nm.

20. The system according to claim 16 wherein the sensor is configured for use in a Raman spectroscopy based method of detecting an analyte that uses any one or combination of Raman scattering, Raman microprobe, confocal Raman microspectrometry, UV-Raman microscopy, surface-enhanced Raman scattering (SERS), surface enhanced resonance Raman spectroscopy (SERRS), tip-enhanced Raman spectroscopy (TERS), hyper-Raman, coherent anti-Stokes Raman spectroscopy (CARS), stimulated Raman scattering, inverse Raman spectroscopy, stimulated gain Raman spectroscopy, three-dimensional Raman spectroscopy, and hyperspectral Raman spectroscopy.

* * * * *